(12) United States Patent
Kakileti et al.

(10) Patent No.: US 11,534,069 B2
(45) Date of Patent: Dec. 27, 2022

(54) SYSTEM AND METHOD FOR ADAPTIVE POSITIONING OF A SUBJECT FOR CAPTURING A THERMAL IMAGE

(71) Applicant: Niramai Health Analytix Pvt Ltd, Bangalore (IN)

(72) Inventors: Siva Teja Kakileti, Kakinada (IN); Geetha Manjunath, Bangalore (IN); Himanshu J. Madhu, Mumbai (IN)

(73) Assignee: NIRAMAI HEALTH ANALYTIX PVT LTD, Bangalore (IN)

( * ) Notice: Subject to any disclaimer, the term of this patent is extended or adjusted under 35 U.S.C. 154(b) by 741 days.

(21) Appl. No.: 16/524,138

(22) Filed: Jul. 28, 2019

(65) Prior Publication Data
US 2020/0352452 A1    Nov. 12, 2020

(30) Foreign Application Priority Data

May 29, 2019    (IN) .............................. 201941021394

(51) Int. Cl.
*G06K 9/00*    (2022.01)
*A61B 5/01*    (2006.01)
(Continued)

(52) U.S. Cl.
CPC ............ *A61B 5/015* (2013.01); *A61B 5/0008* (2013.01); *A61B 5/0013* (2013.01);
(Continued)

(58) Field of Classification Search
CPC ..... A61B 5/015; A61B 5/0008; A61B 5/0013; A61B 5/0077; A61B 5/0091; A61B 5/7267; G06T 7/0012; G06T 7/11; G06T 7/12; G06T 7/13; G06T 7/70; G06T 2207/10048; G06T 2207/20081; G06T 2207/30068; G06T 2207/30096; G06T 2207/30196; G06T 2207/30244; G06T 2207/20084; G06T 7/73; H04N 5/23222; H04N 5/23299; H04N 5/23229; H04N 5/23293; H04N 5/33
See application file for complete search history.

(56) References Cited

U.S. PATENT DOCUMENTS

2008/0025592 A1 * 1/2008 Jerebko ................. G06T 11/005
                                                          382/132
2017/0245762 A1 * 8/2017 Kakileti ................. B25J 19/023
(Continued)

*Primary Examiner* — Tom Y Lu

(57) ABSTRACT

A method for determining a view angle of a thermal image from a user and generating a suggestion to enable the user for adaptive positioning of a subject for capturing the thermal image is provided. The method includes (i) receiving a thermal image of a body of a subject, (ii) automatically determining a view angle of the thermal image from a user using a view angle estimator, (iii) determining an angular adjustment to be made to a view position of the thermal imaging camera or a position of the subject by comparing the determined view angle with a required view angle as per thermal imaging protocol when the thermal image does not meet the required view angle and (iv) generating instructions to the user for adjusting the view position of the thermal imaging camera for capturing a new thermal image at the required view angle as per thermal imaging protocol.

20 Claims, 8 Drawing Sheets

(51) Int. Cl.
*G06T 7/11* (2017.01)
*H04N 5/232* (2006.01)
*G06T 7/13* (2017.01)
*G06T 7/12* (2017.01)
*G06T 7/00* (2017.01)
*A61B 5/00* (2006.01)
*G06T 7/70* (2017.01)

(52) U.S. Cl.
CPC .......... *A61B 5/0077* (2013.01); *A61B 5/0091* (2013.01); *A61B 5/7267* (2013.01); *G06T 7/0012* (2013.01); *G06T 7/11* (2017.01); *G06T 7/12* (2017.01); *G06T 7/13* (2017.01); *G06T 7/70* (2017.01); *H04N 5/23222* (2013.01); *H04N 5/23299* (2018.08); *G06T 2207/10048* (2013.01); *G06T 2207/20081* (2013.01); *G06T 2207/30068* (2013.01); *G06T 2207/30096* (2013.01); *G06T 2207/30196* (2013.01); *G06T 2207/30244* (2013.01)

(56) References Cited

U.S. PATENT DOCUMENTS

| | | | |
|---|---|---|---|
| 2017/0249738 A1* | 8/2017 | Sivakumar | G06T 7/0012 |
| 2017/0270659 A1* | 9/2017 | Venkataramani | G06T 7/11 |
| 2018/0000461 A1* | 1/2018 | Venkataramani | A61B 5/4312 |
| 2018/0000462 A1* | 1/2018 | Venkataramani | A61B 5/015 |

* cited by examiner

SYSTEM AND METHOD FOR ADAPTIVE POSITIONING OF A SUBJECT FOR CAPTURING A THERMAL IMAGE

BACKGROUND

Technical Field

The present invention is directed towards capturing thermal image conformant to standard operating procedure and, more particularly, to a system and method for determining a view angle of a thermal image of a subject from a user to generate a suggestion to capture the thermal image as per standard breast thermography protocol by enabling the use for adaptive positioning of the subject and capturing.

Description of the Related Art

Breast Cancer is among the leading cause of cancer deaths around the world especially in women. Mammography is considered as gold standard for detecting breast cancer. However, it is very costly, painful due to the compression of breast and has a radiation exposure. In the recent years, thermography is emerging as a promising modality for breast cancer screening. Thermography captures the amount of heat radiating from the surface of the body and measures the temperature patterns and distribution on the chest due to high metabolism associated with tumorous growth. There are several advantages of Breast thermography compared to other methods. The breast thermography works on women of all age groups, does not involve any radiation and non-contact and hence painless. The key challenge in breast thermography is the preconditioning and capturing of thermal images of the patient. As tumor cannot be captured always using a single fixed view, the medical expert requires multiple thermal views/videos of the patient for analysis. This multiple view capture is usually done manually by either moving the camera or making the patients turn to required view angles. This kind of capturing requires high expertise and it is observed that low to medium skilled technicians/thermographers are finding difficulty in capturing these thermal images at specified angles due to lack of proper guidance. This also leads to non-standardisation of data across subjects/patients and even may lead to poor performance of breast analysis involving breast segmentation and classification. Typical protocol for breast thermography is to capture five views as five image files named manually by technician. This manual file labelling is error prone and can result in incorrect classification due to wrong image mapping.

Hence, there is a need for an automated guidance system/method to automatically predict the view angle and guide the technician for capturing proper thermal images at required view angles. This can also help in enabling labelling of each frame in the video according to their view angle.

SUMMARY

In view of the foregoing, embodiment herein provides a method for determining a angle of a thermal image from a user and generating a suggestion to enable the user for adaptive positioning of a subject for capturing the thermal image. The method includes (i) receiving a thermal image of a body of a subject, which represents the temperature distribution on the body of the subject as pixels in the thermal image with a highest temperature value being displayed in a first color and pixels with a lowest temperature value being displayed in a second color, pixels with temperature values between the lowest and highest temperature values being displayed in gradations of color between the first and second colors; (ii) automatically determining a view angle of the thermal image from a user using a view angle estimator; (iii) determining, using a machine learning model, an angular adjustment to be made to a view position of the thermal imaging camera or a position of the subject by comparing the determined view angle with a required view angle as per thermal imaging protocol when the thermal image does not meet the required vie angle as per thermal imaging protocol; and (iv) generating a set of instructions to the user for adjusting the view position of the thermal imaging camera for capturing a new thermal image at the required view angle as per thermal imaging protocol. The thermal image is captured by a thermal imaging camera that includes an array of sensors, a lens and a specialized processor. The array of sensors converts infrared energy into electrical signals on a per-pixel basis. The lens focuses the infrared energy from the subject's body onto the array of sensors. The array of sensors detects temperature values from the subject's body. The specialized processor processes the detected temperature values into at least one block of pixels to generate the thermal image.

In an embodiment, the method includes the step of providing the new captured thermal image along with determined view angle for automatic breast segmentation followed by an automatic tumor detection method to detect cancerous tissue and/or non-cancerous tissue within a breast area of the subject.

Its another embodiment, the method includes, step of implementing an automatic segmenting technique to segment the breast area of the subject in the thermal image by (i) determining an outer side contour of an outline of a boundary of the breast area of the subject from a body silhouette, (ii) determining an inner side boundary of the breast area from the body silhouette and the view angle of the thermal image, (iii) determining an upper boundary of the breast area by determining a lower boundary of an isotherm of axilla of the subject, (iv) determining a lower boundary of the breast area by determining an upper boundary of an isotherm of infra-mammary fold of the person and (v) segmenting the breast area of the, subject by connecting above determined breast boundaries to segment the breast from surrounding tissue in the thermal image.

In yet another embodiment, the implementation of the automatic segmenting technique to segment the breast area of the subject in the thermal image includes (i) training a deep learning model by providing a plurality of thermal images as an input and the corresponding segmentation as an output to obtain the trained deep learning model and (ii) providing the new captured thermal image to the trained deep learning model to predict a final segmentation map.

In yet another embodiment, the view angle estimator includes a regression machine learning model that determines an approximate view angle of the subject with respect to the camera using the thermal image.

In yet another embodiment, the view angle estimator includes a tagging classifier. The tagging classifier includes a machine learning model that determines the view of the thermal image and classifies the thermal image as one of the discrete views such as a right lateral view, a right oblique view, a frontal view, a left lateral view or a left oblique view as per the thermal imaging protocol.

In yet another embodiment, the set of instructions is provided to at least one of a robotic arm holding the camera, an electronically controlled camera stand or an electronically controlled rotating chair to automatically positions itself to the suggested angular adjustment for capturing the new thermal image at the required view angle.

In yet another embodiment, the view angle estimator automatically captures the new thermal image at the required view angle without user's intervention.

In yet another embodiment, the method includes the step of displaying at least one of the determined view angle of the thermal image or the segmented breast area on a visualization screen.

In yet another embodiment, the automatic tumor detection method includes (i) determining a percentage of pixels $p_1$ within said selected region of interest with a temperature $T^1_{pixel}$, where $T_2 \leq T^1_{pixel} \leq T_1 m$, (ii) determining a percentage of pixels $p_2$ within said selected region of interest with a temperature $T^2_{pixel}$, where $T_3 \leq T^2_{pixel}$ and (iii) determining a ratio $p_3 = P_{edge}/P_{block}$, where $P_{edge}$ is a number of pixels around a border of a suspected tumor within said region of interest, and $P_{block}$ is a number of pixels in the perimeter of said region of interest. The $T_1$, $T_2$ and $T_3$ are temperature threshold obtained from temperature distribution In yet another embodiment, the method includes the step of determining whether a suspected tumor region as one of: said cancerous tissue, said non-cancerous using a decision rule R. The decision rule R is based on any combination of: $R_1$, $R_2$, $R_3$, where: $R_1=(p_1>Threshold_1)$, $R_2=(p_2>Threshold_2)$, and $R_3=(p_3>Threshold_3)$.

In yet another embodiment, the view angle estimator automatically labels the thermal image with a label signifying its discrete view angle. In yet another embodiment, the method comprises the step of correcting view angle errors in said thermal imaging protocol by modifying the data object properties comprising filenames using said label.

In yet another embodiment, the view angle estimator is applied on a thermal image that is obtained by selecting a single image frame of a thermal video or a live stream thermal video. The thermal video or the live stream thermal video is captured using the thermal imaging camera.

In yet another embodiment, the view angle estimator includes a tagging classifier that selects a thermal image that meets the required view angle from one or more thermal images that are obtained from a thermal video or live stream thermal video.

In yet another embodiment, the set of instructions includes at least one of a text, a visual or audio for capturing the new thermal image at the required view angle.

In another aspect, a system for determining a view angle of a thermal image from a user and generating a suggestion to enable the user for adaptive positioning of a subject for capturing the thermal image is provided. The system includes a storage device, and a processor retrieving machine-readable instructions from the storage device which, when executed by the processor, enable the processor to (i) receive a thermal image of a body of a subject, which represents the temperature distribution on the body of the subject as pixels in the thermal image with a highest temperature value being displayed in a first color and pixels with a lowest temperature value being displayed in a second color, pixels with temperature values between the lowest and highest temperature values being displayed in gradations of color between the first and second colors; (ii) automatically determine a view angle of the thermal image; (iii) determine an angular adjustment to be made to a view position of the thermal imaging camera or a position of the subject by comparing the determined view angle with a required view angle as per thermal imaging protocol when the thermal image does not meet the required view angle as per thermal imaging protocol, using a machine learning model; (iv) generate a set of instructions to the user for adjusting the view position of the thermal imaging camera for capturing a new thermal image at the required view angle as per thermal imaging protocol. The thermal imaging camera includes an array of sensors, a lens and a specialized processor. The array of sensors converts infrared energy into electrical signals on a per-pixel basis. The lens focuses the infrared energy from the subject's body onto the array of sensors. The array of sensors detects temperature values from the subject's body. The specialized processor processes the detected temperature values into at least one block of pixels to generate the thermal image.

In an embodiment, the system provides the new captured thermal image along with determined view angle to the view angle determination unit for automatic breast segmentation followed by an automatic tumor detection method to detect cancerous tissue and/or non-cancerous tissue within a breast area of the subject.

In another embodiment, the system implements an automatic segmenting technique to segment the breast area of the subject in the thermal image by (i) determining an outer side contour of an outline of a boundary of the breast area of the subject from a body silhouette, (ii) determining an inner side boundary of the breast area from the body silhouette and the view angle of the thermal image, (iii) determining an upper boundary of the breast area by determining a lower boundary of an isotherm of axilla of the subject, (iv) determining a lower boundary of the breast area by determining an upper boundary of an isotherm of infra-mammary fold of the person and (v) segmenting the breast area of the subject by connecting above determined breast boundaries to segment the breast from surrounding tissue in the thermal image.

In another embodiment, the system implements the automatic segmenting technique to segment the breast area of the subject in the thermal image includes training a deep learning model by providing a plurality of thermal images as an input and the corresponding segmentation as an output to obtain the trained deep learning model and providing the new captured thermal image to the trained deep learning model to predict a final segmentation map.

In yet another embodiment, the system provides set of instructions to at least one of a robotic arm holding the camera, an electronically controlled camera stand or an electronically controlled rotating chair to automatically positions itself to the suggested angular adjustment for capturing the new thermal image at the required view angle.

The system ensures correct segmentation of the breasts region with better accuracy. The system enables automatic selection of required views from the videos and guides a technician to capture the perfect view of the thermal image. The system may automate the thermal image capturing by obtaining feedback from the tagging classifier/the view angle estimator. A set of frames from a video may be passed as a batch input to the system and the system may predict a view angle to enable segmentation of the breast region in all frames. The system performs an automated image capturing with minimal or no human intervention during image capture.

These and other aspects of the embodiments: herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will, be better understood from the following detailed description with reference to the drawings, in which.

DETAILED DESCRIPTION OF PREFERRED EMBODIMENTS

Figure 1:
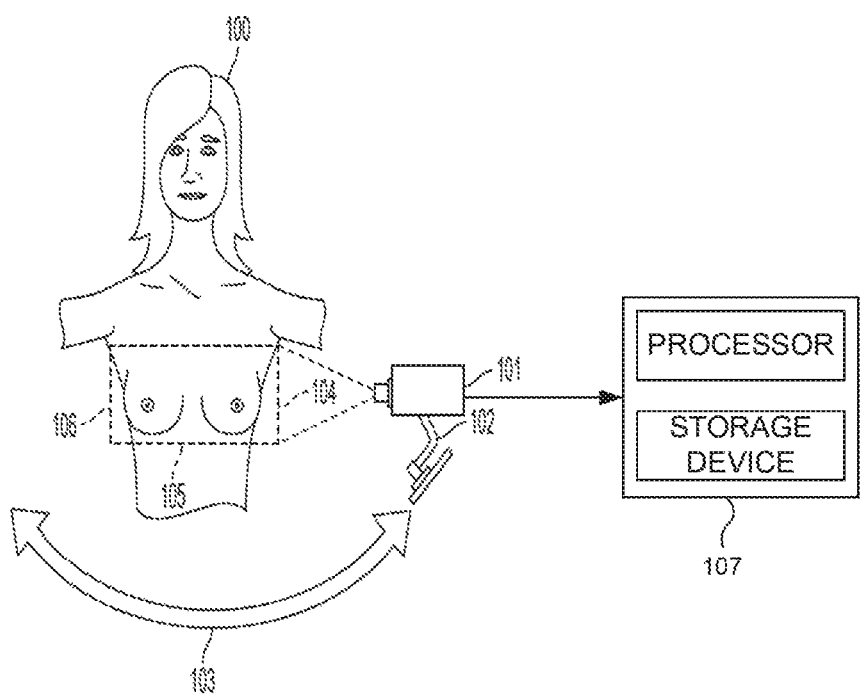
FIG. 1 illustrates an example female patient with a thermal imaging camera mounted on a slidable and axially rotatable robotic arm for moving the thermal camera along a semi-circular trajectory from side-to-side in front of the patient according to an embodiment herein.

The embodiments herein and the various, features and advantageous details thereof are explained more fully with reference to the non-lining embodiments that are illustrated in the accompanying drawings and detailed in the following description, Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned there remains a need for a system, and a method for determining a view angle of a thermal image from a user and generating a suggestion to enable the user for adaptive positioning of a subject for capturing the thermal image. Referring now to the drawings, and more particularly to FIGS. 1 through 8, where similar reference characters denote corresponding features consistently throughout the figures, there are shown preferred embodiments.

A "person" refers to either a male or a female. Gender pronouns are not to be viewed as limiting the scope of the appended claims strictly to females. Moreover, although the term "person" or "patient" is used interchangeably throughout this disclosure, it should be appreciated that the person undergoing breast cancer screening may be something other than a human such as, for example, a primate. Therefore, the use of such terms is not to be viewed as limiting the scope of the appended claims to humans.

A "breast area" refers to tissue of the breast and may further include surrounding tissue as is deemed appropriate for breast cancer screening. Thermal images are the capture of the breast area in various view angles which include a mediolateral view (center chest), a mediolateral oblique (angular) view, and a lateral (side) view, as are generally understood in the medical imaging arts. It should be appreciated that the mediolateral view is a supplementary mammographic view which generally shows less breast tissue and pectoral muscle than the mediolateral oblique view. FIG. 1 shows the breast area of a female 100. It should be appreciated that the patient may be stationary while the camera moves about the patient, or the patient can move while the camera remains stationary, or the patient and the camera, may move to capture the appropriate view angles as desired.

A "thermal camera" refers to either a still camera or a video camera with a lens that focuses infrared energy from objects in a scene onto an array of specialized sensors which convert infrared energy across a desired thermal wavelength band into electrical signals on a per-pixel basis and which output an array of pixels with colours that correspond to temperatures of the objects in the image.

A "thermographic image" or simply a "thermal image" is an image captured by a thermal camera. The thermographic image comprises an array of color pixels with each color being associated with temperature. Pixels with a higher temperature value are displayed in the thermal image in a first color and pixels with a lower temperature value are displayed in a second color. Pixels with temperature values between the lower and higher temperature values are, displayed in gradations of color between the first and second colors.

"Receiving a thermal image" of a patient for cancer screening is intended to be widely construed and includes retrieving, capturing, acquiring, or otherwise obtaining video image frames.

"Analyzing the thermographic image" means to identify a plurality of points (PN) in the image.

A "software interface tool" is a composite of functionality for tumor detection and/or tumor classification using a plurality of user-selectable objects displayed on a display device such as a touchscreen display. One embodiment of a software interface tool which implements a tumor detection method is disclosed in commonly owned and co-pending U.S. patent application Ser. No. 14/668,178, entitled: "Software Interface Tool For Breast Cancer Screening" by Krithika Venkataramani et al. Another embodiment of a software interface tool which implements a tumor classification method is disclosed in commonly owned and co-pending U.S. patent application Ser. No. 15/053,767, entitled: "Software Interface Tool For Breast Cancer Screening", by Gayatri Sivakumar et al. Various embodiments of the software interface tool perform manual, semi-automatic, and automatic selection of a block of pixels in the thermal image for screening.

FIG. 1 illustrates an example female patient with a thermal imaging camera mounted on a slidable and axially rotatable robotic arm for moving the thermal camera along a semi-circular trajectory from side-to-side in front of the patient according to an embodiment herein. The thermal imaging camera 101 is mounted on a slidable and axially rotatable robotic arm 102 capable of moving the thermal imaging camera along a semi-circular trajectory 103 in the front of the patient/subject from side-to-side such that thermographic images may be captured in a right-side view 104, a front view 105, and a left-side view 106, and various oblique angles in between. The thermal imaging camera 101 can be a single-band infrared camera, a multi-band infrared camera in the thermal range, and a hyperspectral infrared camera in the thermal range. The resolution of the thermal imaging camera 101 is effectively the size of the pixel. Smaller pixels mean that the resulting image have a higher resolution and thus better spatial definition. Although the thermal imaging camera 101 offers a relatively large dynamic range of temperature settings, it is preferable that the camera's temperature range be relatively small, centered around the person's body surface temperature so that small temperature variations are amplified in terms of pixel color changes in order to provide a better measure of temperature variation. Thermal imaging cameras are readily available in various streams of commerce. The thermal imaging camera 101 is communicatively connected to an adaptive view angle positioning system 107 which process the thermal image captured by the thermal imaging camera 101 for determining a view angle of the thermal image from a user and for generating a suggestion to enable the user/robotic arm for adaptive positioning of a patient/subject for capturing the thermal image.

Figure 2:
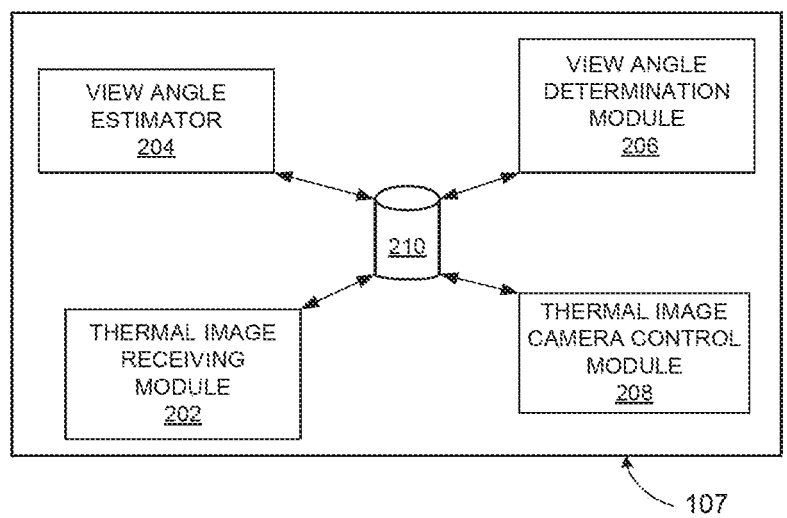
FIG. 2 illustrates an exploded view of an adaptive view angle positioning system for determining a view angle of a thermal image from a user and for generating a suggestion to enable the user for adaptive positioning of a subject for capturing the thermal image according to an embodiment herein.

FIG. 2 illustrates an exploded view of an adaptive view angle positioning system for determining a view angle of a thermal image from a user and for generating a suggestion to enable the user for adaptive positioning of a subject for capturing the thermal image according to an embodiment herein. The adaptive view angle positioning system 107 includes a thermal image receiving module 202, a view angle estimator 204, a view angle determination module 206 and a thermal camera control module 208. The thermal image receiving module 202 receives a thermal image of a body of a subject/patient. The thermal image represents the temperature distribution on the body of the subject as pixels in the thermal image with a highest temperature value being displayed in a first color and pixels with a lowest temperature value being displayed in a second color, pixels with temperature values between the lowest and highest temperature values being displayed in gradations of color between the first and second colors. In an embodiment, the thermal image is captured using a thermal imaging camera which is connected with the adaptive view angle positioning system 107. In an embodiment, the thermal imaging camera includes an array of sensors, a lens and a specialized processor. The array of sensors converts infrared energy into electrical signals on a per-pixel basis. The lens focuses the infrared energy from the subject's body onto the array of sensors. The array of sensors detects temperature values from the subject's body. The specialized processor processes the detected temperature values into at least one block of pixels to generate the thermal image. The view angle estimator 204 automatically determines a view angle of the thermal image. In an embodiment, the view angle of the thermal image is determined using a tagging classifier that selects a thermal image that meets the required view angle from one or more thermal images that are obtained from a thermal video or a live stream thermal video. The tagging classifier includes a machine learning model that determines the view of the thermal image and classifies the thermal image as one of the discrete views such as a right lateral view, a right oblique view, a frontal view, a left lateral view or a left oblique view as per the thermal imaging protocol. In an embodiment, the thermal imaging protocol includes at least one steps of (i) cooling the thermal image for a particular time interval, (ii) positioning the subject in such a way that the thermal image of the complete chest area with axilla is visible, (iii) focusing the thermal image of the subject for capturing the high resolution thermal image of the subject, (iv) capturing the thermal image of the subject in at least one of front view, left oblique view, left lateral view, right oblique view or right lateral view or (v) providing the captured thermal image of the subject to the system for further analysis. The view angle estimator 204 automatically labels the thermal image with a label signifying its discrete view angle. The label may include a file name for the thermal image. In an embodiment, the view angle estimator 204 is applied on a thermal image that is obtained by selecting a single image frame of a thermal video or a live stream thermal video. In another embodiment, the view angle estimator 204 includes a regression machine learning model that determines an approximate view angle of the subject with respect to the thermal imaging camera using the thermal image. The view angle estimator 204 includes a convolution neural network regressor to estimate the view angle directly from the thermal image.

The view angle determination module 206 determines an angular adjustment to be made to a view position of the thermal imaging camera or a position of the subject using a machine learning model. The view angle determination module 206 compares the determined view angle with a required view angle as per thermal imaging protocol when the thermal image does not meet the required view angle as per thermal imaging protocol to determine an angular adjustment to be made to a view position of the thermal imaging camera or a position of the subject. The thermal camera control module 208 provides set of instructions to technician or at least one of a robotic arm holding the camera, an electronically controlled camera stand or an electronically controlled rotating chair to automatically positions itself to the suggested angular adjustment for capturing the new thermal image at the required view angle as per thermal image protocol. The set of instructions includes at least one of a text, a visual or audio for capturing the new thermal image at the required view angle.

The adaptive view angle positioning system 107 provides the new captured thermal image along with determined view angle for automatic breast segmentation followed by an automatic tumor detection method to detect cancerous tissue and/or non-cancerous tissue within a breast area of the subject. In an, embodiment, the view angle estimator automatically captures the new thermal image at the required view angle without user's intervention. In an embodiment, the adaptive view angle positioning system 107 adapted with a segmentation system or module that implements an automatic segmenting technique to segment the breast area of the subject in the thermal image by determining at least one of (i) an outer side contour of an outline of a boundary of the breast area of the subject from a body silhouette (ii) an inner side boundary of the breast area from the body silhouette and the view angle of the thermal image, (iii) an upper boundary of the breast area by determining a lower boundary of an isotherm of axilla of the subject, or (iv) a lower boundary of the breast area by determining an upper boundary of an isotherm of infra-mammary fold of the person. The adaptive view angle positioning system 107 segments the breast area of the subject by connecting above determined breast boundaries to segment the breast from surrounding tissue in the thermal image.

In an embodiment, the adaptive view angle positioning system 107 may includes a machine learning model for automatically segmenting the breast area of the subject in the thermal image. The machine learning model is trained by providing a plurality of thermal images as an input and the corresponding segmentation as an output to obtain the trained deep learning model. The adaptive view angle positioning system 107 provides the new captured thermal image to the trained deep learning model to predict a final segmentation map. The adaptive view angle positioning system 107 may display at least one of the determined view angle of the thermal image or the segmented breast area on a visualization screen. In another embodiment, the automatic tumor detection includes the steps of (i) determining a percentage of pixels pi within said selected region of interest with a temperature $T^1_{pixel}$, where $T_2 \leq T^1_{pixel} \leq T_1$, (ii) determining a percentage of pixels $p_2$ within said selected region of interest with a temperature $T^2_{pixel}$, where $T_3 \leq T^2_{pixel}$ and (iii) determining a ratio $p_3 = P_{edge}/P_{block}$, where $P_{edge}$ is a number of pixels around a border of a suspected tumor within said region of interest, and $P_{block}$ is a number of pixels in the perimeter of the region of interest. The adaptive view angle positioning system 107 includes a malignancy classifier that determines whether a suspected tumor region as one of: said cancerous tissue, said non-cancerous using a decision rule R. The decision R is based on any combination of: $R_1$, $R_2$, $R_3$, where: $R_1 = (p_1 > \text{Threshold}_1)$, $R_2 = (p_2 > \text{Threshold}_2)$, and $R_3 = (p_3 > \text{Threshold}_3)$.

Figure 3:
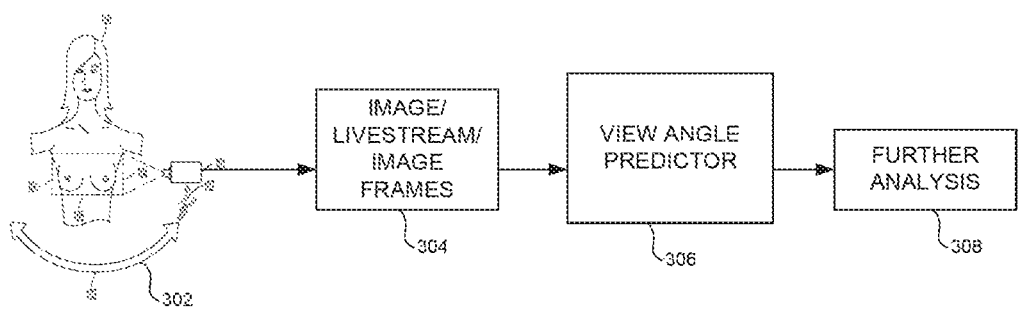
FIG. 3 illustrates an exemplary process flow of an automated Region of Interest (ROI) analysis of a thermal image from a user using an adaptive view angle positioning system according to an embodiment herein.

FIG. 3 illustrates an exemplary process flow of automated Region of Interest (ROI) analysis of a thermal image from a user using an adaptive view angle positioning system according to an embodiment herein. At step 302, the thermal image is captured using a thermal imaging camera. In some embodiment, the thermal image may be received or retrieved from a remote device over a network, or from a media such as a CDROM or DVD. The thermal image may be downloaded from a web-based system or an application which makes a video available for processing, in accordance with the methods disclosed herein. The thermal image may also be received from an application such as those which are available for handheld cellular devices and processed on the cell phone or other handheld computing devices such as an iPad or Tablet-PC. The thermal image may be received directly from a memory or storage device of the imaging device that is used to capture that thermal image or a thermal video.

At step 304, the thermal image is obtained by selecting a single image frame of a thermal video or a livestream thermal video. The thermal video or the livestream thermal video is captured using the thermal imaging camera. At step 306, the thermal image that meets the required view angle from one or more thermal images that are obtained from the thermal video oil live stream thermal video is selected using a tagging classifier. The tagging classifier includes a machine learning model that determines the view of the thermal image and classifies the thermal image as one of the discrete views such as a right lateral view, a right oblique view, a frontal view, a left lateral view or a left oblique view as per the thermal imaging protocol. At step 308, the selected thermal images are provided to the adaptive view angle positioning system for further analysis.

Figure 4:
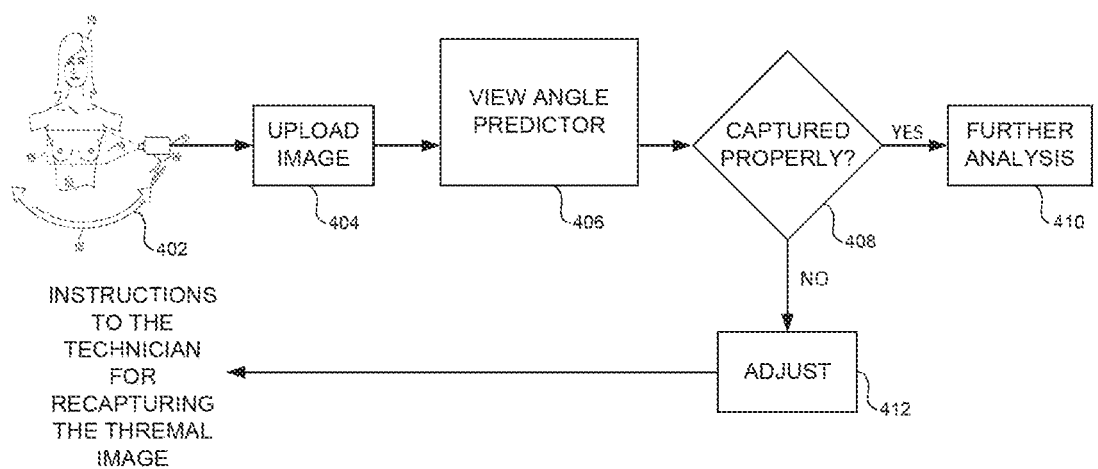
FIG. 4 illustrates an exemplary process flow of an offline view angle determination of a thermal image from a user using an adaptive view angle positioning system according to an embodiment herein.

FIG. 4 illustrates an exemplary process flow of an offline view angle determination of a thermal image from a user using an adaptive view angle positioning system according to an embodiment herein. At step 402, the thermal image is captured using a thermal imaging camera. At step 404, the thermal image N uploaded into the adaptive view angle positioning system. At step 406, the view angle of the uploaded thermal, image from a user is determined. At step 408, it is determined whether the thermal image is captured correctly by comparing the determined view angle with a required view angle as per thermal imaging protocol when the thermal image does not meet the required view angle as per thermal imaging protocol to determine an angular adjustment to be made to a view position of the thermal imaging camera or a position of the subject. At step 410, the thermal image N provided for further analysis, for example segmentation and/or breast cancer screening, if the thermal image is captured with a required view angle as per the thermal imaging protocol. If not, at step 412 a set of instructions to the user is generated for adjusting the view position of the thermal imaging camera for capturing a new thermal image at the required view angle as per thermal imaging protocol.

Figure 5:
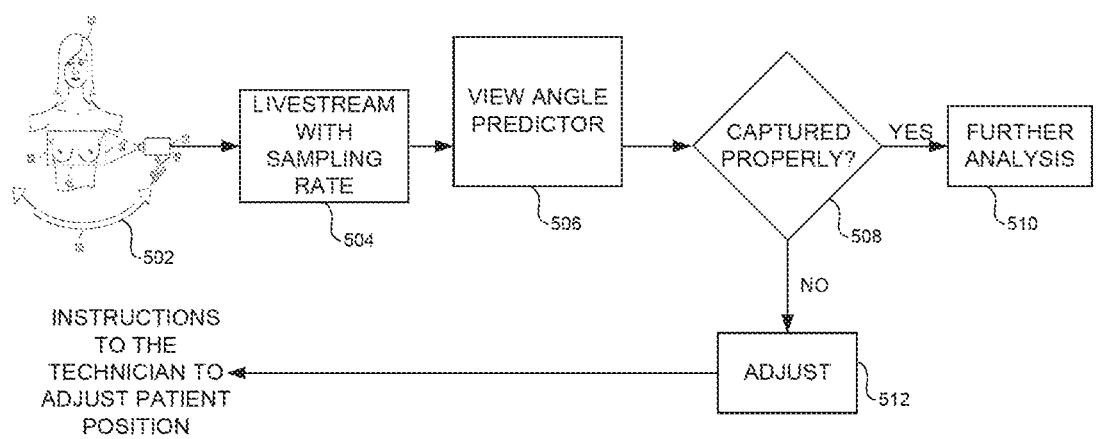
FIG. 5 illustrates an exemplary process flow of a live stream view angle determination of a thermal image from a user using an adaptive view angle positioning system according to an embodiment herein.

FIG. 5 illustrates an exemplary process flow of a live stream view angle determination of a thermal image from a user using an adaptive view angle positioning system according to an embodiment herein. At step 502, the livestream with sequential frames (e.g. thermal image/video) is captured using a thermal imaging camera. At step 504, a sample rate or adaptive sampling algorithms are applied to analyze selected frames of the thermal video instead of all frames to determine the view angle. At step 506, the view angle of the sampled thermal frame(s) from a user is determined. At step 508, it is determined whether the thermal frame(s) are captured correctly by comparing the determined view angles with a required view angle as per thermal imaging protocol when the thermal frame(s) do not meet the required view angle as per thermal imaging protocol to determine an angular adjustment to be made to a view position of the thermal imaging camera or a position of the subject. At step 510, the thermal framers) are provided for further analysis, for example segmentation and/or breast cancer screening, if the thermal frame(s) are captured with a required view angle as per the thermal imaging protocol. If not, at step 512, a set of instructions to the user is generated for adjusting the view position of the thermal imaging camera for capturing a new thermal image at the required view angle as per thermal imaging protocol.

Figure 6:
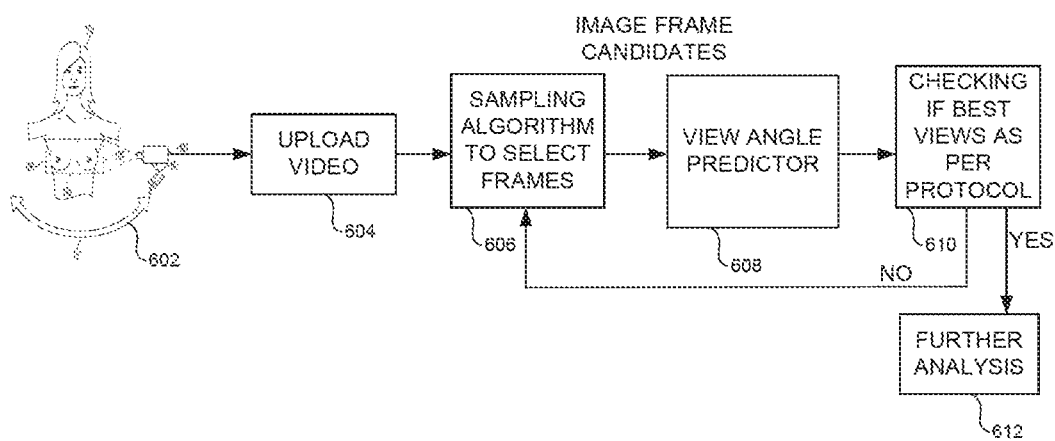
FIG. 6 illustrates an exemplary process flow of a view angle determination using an adaptive view angle positioning system to select a view with adaptive sampling to reduce image frame candidates according to an embodiment herein.

FIG. 6 illustrates an exemplary process flow of a view angle determination using an adaptive view angle positioning system to select a view with adaptive sampling to reduce image frame candidates according to an embodiment herein. At step 602, the thermal video is captured using a thermal imaging camera. At step 604, the thermal video is uploaded to the adaptive view angle positioning system. At step 606, a sample rate or adaptive sampling algorithms are applied to analyze selected frames of the thermal video instead of all frames to determine the view angle. At step 608, the view angles of the selected frames are determined. At step 610, it is determined whether the thermal frames match the requited view angles as per thermal imaging protocol by comparing the determined view angles with the required vie angles as per thermal imaging protocol. At step 612, the thermal frames are provided for further analysis, for example segmentation and/or breast cancer screening, if the thermal frames are as per the thermal imaging protocol. If not, it toes back to step 606 to adjust the sampling rate.

In an embodiment, the required thermal frames selected from a captured thermal video of a subject (e.g. frames to be considered 0, ±45, ±90) are used for automated analysis. The input to the adaptive view angle positioning system is the entire frames from the thermal video or sampled frame from any adaptive sampling algorithm. The adaptive view angle positioning system determines the best frames corresponding to the required view angles. In an embodiment, the adaptive view angle positioning system determines the view angle of the thermal image from a user based on specific angles that is used for analysis such as breast cancer screening.

Figure 7:
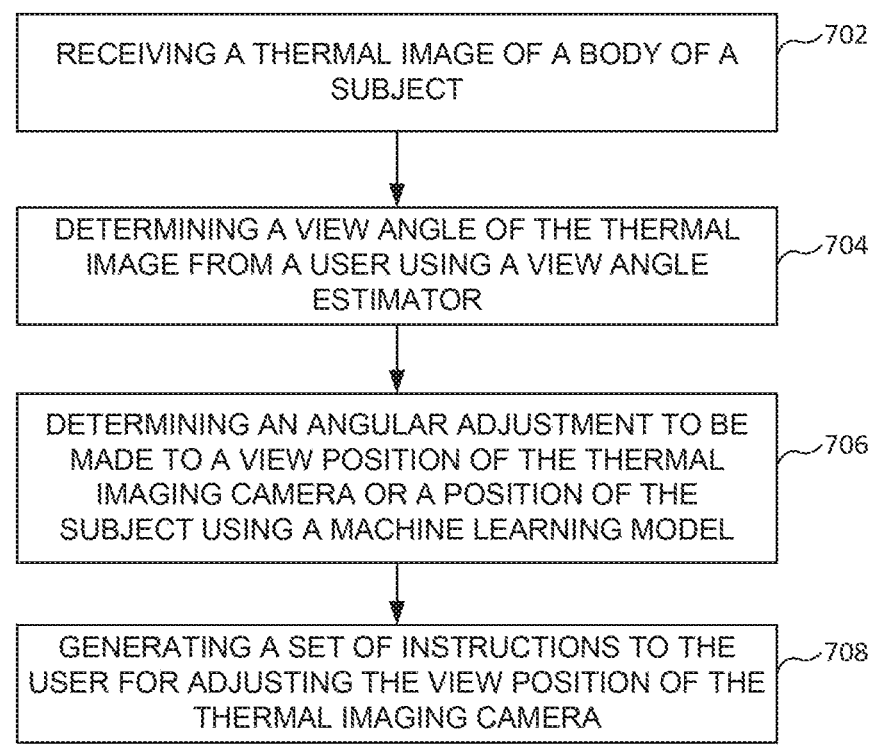
FIG. 7 illustrates a flow diagram of one embodiment of the present method for determining a view angle of a thermal image from a user and generating a suggestion to enable the user for adaptive positioning of a subject for capturing the thermal image according to an embodiment herein.

FIG. 7 illustrates a flow diagram of one embodiment of the present method for determining a view angle of a thermal image from a user and generating a suggestion to enable the user for adaptive positioning of a subject for capturing the thermal image according to an embodiment herein. At step 702, a thermal image of a body of a subject is received. The thermal image represents the temperature distribution on the body of the subject as pixels in the thermal image with a highest temperature value being displayed in a first color and pixels with a lowest temperature value being displayed in a second color. pixels with temperature values between the lowest and highest temperature values being displayed in gradations of color between the first and second colors. At step 704, a view angle of the thermal image from a user is automatically determined using a view angle estimator. At step 706, an angular adjustment to be made to a view position of the thermal imaging camera or a position of the subject is determined using a machine learning model by comparing the determined view angle with a required view angle as per thermal imaging protocol when the thermal image does not meet the required view angle as per thermal imaging protocol. At step 708, a set of instructions is generated to the user for adjusting the view position of the thermal imaging camera for capturing a new thermal image at the required view angle as per thermal imaging protocol.

Figure 8:
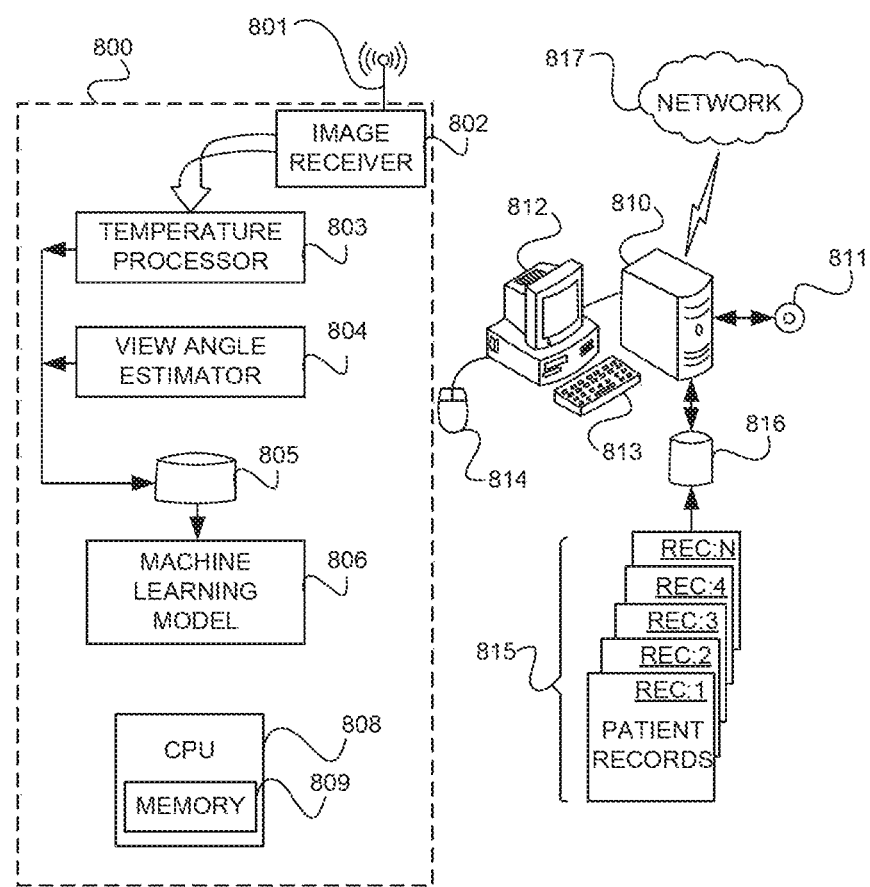
FIG. 8 illustrates a block diagram of one example adaptive view angle positioning system/image processing system for processing a thermal image in accordance with the embodiments described with respect to the flow diagram of FIG. 7 according to an embodiment herein.

FIG. 8 illustrates a block diagram of one example adaptive view angle positioning system/image processing system 800 for processing a thermal image in accordance with the embodiments described with respect to the flow diagram of FIG. 7 according to an embodiment herein. Image Receiver 802 wirelessly receives the video via antenna 801 having been transmitted thereto from the video/thermal imaging device 101 of FIG. 1. Temperate Processor 803 performs a temperature-based method to detect pixels in the received image. View angle estimator 804 determines a view angle of the thermal image front a user. Both Modules 803 and 804 store their results to storage device 805 Machine learning model 806 retrieves the results of from storage device 805 and proceeds to determine an angular adjustment to be made to a view position of the thermal imaging camera 101 or a position of the subject by comparing the determined view angle with a required view angle as per thermal imaging protocol when the thermal image does not meet the required view angle as per thermal imaging protocol. The machine learning model 806 generates a set of instructions to the user for adjusting the view position of the thermal imaging camera 101 for capturing the new thermal image at the required view angle as per thermal imaging protocol. Central Processing Unit 808 retrieves machine readable program instructions from a memory 809 and is provided to facilitate the functionality of any of the modules of the system 800. CPU 808, operating alone or in conjunction with other processors, may be configured to assist or otherwise perform the functionality of any of the modules or processing units of the system 800 as well as facilitating communication between the system 800 and the workstation 810.

System 800 is shown having been placed in communication with a workstation 810. A computer case of the workstation houses various components such as a motherboard with a processor and memory, a network card, a video card a hard drive capable of reading/writing to machine readable media 811 such as a floppy disk, optical disk, CD-ROM, DVD, magnetic tape, and the like, and other software and hardware needed to perform the functionality of a computer workstation. The workstation further includes a display device 812, such as a CRT, LCD, or touch screen device, for displaying information, images, view angles, and the like. A user can view any of that information and make a selection from menu options displayed thereon. Keyboard 813 and mouse 814 effectuate a user input. It should be appreciated that the workstation has an operating system and other specialized software configured to display alphanumeric values, menus, scroll bars, dials, slideable bars, pull-down options, selectable buttons, and the like, for entering, selecting, modifying, and accepting information needed for processing in accordance with the teachings hereof. The workstation is further enabled to display thermal images, view angle of the thermal images and the like as they are derived. A user or technician may use the user interface of the workstation to set parameters, view/adjust the view angle, and adjust various aspects of the view angle estimation being performed, as needed or as desired, depending on the implementation. Any of these selections or inputs may be stored/retrieved to storage device 811. Default settings can be retrieved from the storage device. A user of the workstation is also able to view or manipulate any of the data in the patient records, collectively at 815, stored in database 816. Any of the received images, results, determined view angle, and the like, may be stored to a storage device internal to the workstation 810. Although shown as a desktop computer, the workstation can be a laptop, mainframe, or a special purpose computer such as an AMC, circuit, or the like.

Any of the components of the workstation may be placed in communication with any of the modules and processing units of system 800. Any of the modules of the system 800 can be placed in communication with storage devices 805, 816 and 106 and/or computer readable media 811 and may store/retrieve there from data, variables, records, parameters, functions, and/or machine readable/executable program instructions, as needed to perform their intended functions. Each of the modules of the system 800 may be placed in communication with one or more remote devices over network 817. It should be appreciated that some or all of the functionality performed by any of the modules or processing units of the system 800 can be performed, in whole or in part, by the workstation. The embodiment shown is illustrative and should not be viewed as limiting the scope of the appended claims strictly to that configuration. Various modules may designate one or more components which may, in turn, comprise software and/or hardware designed to perform the intended function.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope.

We claim:

1. A method for determining a view angle of a thermal image from a user and generating a suggestion to enable the user for adaptive positioning of a subject for capturing the thermal image, characterized in that the method comprising:
receiving a thermal image of a body of a subject, which represents the temperature distribution on the body of the subject as pixels in the thermal image with a highest temperature value being displayed in a first color and pixels with a lowest temperature value being displayed in a second color, pixels with temperature values between the lowest and highest temperature values being displayed in gradations of color between the first and second colors, wherein the thermal image is captured by a thermal imaging camera, wherein the thermal imaging camera comprising:
an array of sensors that converts infrared energy into electrical signals on a per-pixel basis;
a lens that focuses the infrared energy from the subject's body onto the array of sensors, wherein the array of sensors detects temperature values from the subject's body; and
a specialized processor that processes the detected temperature values into at least one block of pixels to generate the thermal image,
automatically determining a view angle of the thermal image from a user using a view angle estimator;
determining, using a machine learning model, an angular adjustment to be made to a view position of the thermal imaging camera or a position of the subject by comparing the determined new angle with a required view angle as per thermal imaging protocol when the thermal image does not meet the required view angle as per thermal imaging protocol; and
generating a set of instructions to the user for adjusting the view position of the thermal imaging camera for capturing a new thermal image at the required view angle as per thermal imaging protocol.

2. The method of claim 1, wherein the method comprises step of providing the new captured thermal image along with determined view angle for automatic breast segmentation followed by an automatic tumor detection method to detect cancerous tissue and/or non-cancerous tissue within a breast area of the subject.

3. The method of claim 2, wherein the method comprises step of implementing an automatic segmenting technique to segment the breast area of the subject in the thermal image by:
determining an outer side contour of an outline of a boundary of the breast area of the subject from a body silhouette;
determining an inner side boundary of the breast area from the body silhouette and the view angle of the thermal image;
determining an upper boundary of the breast area by determining a lower boundary of an isotherm of axilla of the subject;
determining a lower boundary of the breast area by determining an upper boundary of an isotherm of infra-mammary fold of the person; and
segmenting the breast area of the subject by connecting above determined breast boundaries to segment the breast from surrounding tissue in the thermal image.

4. The method of claim 2, wherein the implementation of the automatic segmenting technique to segment the breast area of the subject in the thermal image comprises:
training a deep learning model by providing a plurality of thermal images as an input and the corresponding segmentation as an output to obtain the trained deep learning model; and
providing the new captured thermal image to the trained deep learning model to predict a final segmentation map.

5. The method of claim 1, wherein the view angle estimator comprises a regression machine learning model that determines an approximate view angle of the subject with respect to the camera using the thermal image.

6. The method of claim 1, wherein the view angle estimator comprises a tagging classifier, wherein the tagging classifier comprises a machine learning model that determines the view of the thermal image and classifies the thermal image as one of discrete views such as a right lateral view, a right oblique view, a frontal view, a left lateral view or a left oblique view as per the thermal imaging protocol.

7. The method of claim 1, wherein said set of instructions is provided to at least one of a robotic arm holding the camera, an electronically controlled camera stand or an electronically controlled rotating chair to automatically positions itself to the suggested angular adjustment for capturing the new thermal image at the required view angle.

8. The method of claim 1, wherein the view angle estimator automatically captures the new thermal image at the required view angle without user's intervention.

9. The method of claim 3, wherein the method comprises the step of displaying at least one of the determined view angle of the thermal image or the segmented breast area on a visualization screen.

10. The method of claim 2, wherein said automatic tumor detection method comprises:
determining a percentage of pixels $p_1$ within said selected region of interest with a temperature $T^1_{pixel}$, where $T_2 \leq T^1_{pixel} \leq T_1$;
determining a percentage of pixels $p_2$ within said selected region of interest with a temperature $T^2_{pixel}$, where $T_3 \leq T^2_{pixel}$; and
determining a ratio $p_3 = P_{edge}/P_{block}$, where $P_{edge}$ is a number of pixels around a border of a suspected tumor within said region of interest, and $P_{block}$ is a number of pixels in the perimeter of said region of interest, wherein $T_1$, $T_2$ and $T_3$ are temperature threshold obtained from temperature distribution.

11. The method of claim 2, wherein the method comprises determining whether a suspected tumor region as one of: said cancerous tissue, said non-cancerous using a decision rule R, wherein said decision rule R is based on any combination of: $R_1$, $R_2$, $R_3$, where: $R_1=(p_1>Threshold_1)$, $R_2=(p_2>Threshold_2)$, and $R_3=(p_3>Threshold_3)$.

12. The method of claim 1, wherein the view angle estimator automatically labels the thermal image with a label signifying its discrete view angle.

13. The method of claim 12, wherein the method comprises correcting view angle errors in said thermal imaging protocol by modifying the data object properties comprising filenames using said label.

14. The method of claim 1, wherein the view angle estimator is applied on a thermal age that is obtained by selecting a single image frame of a thermal video or a live stream thermal video, wherein the thermal video or the live stream thermal video is captured using the thermal imaging camera.

15. The method of claim 14, wherein the view angle estimator comprises a tagging classifier that selects a thermal image that meets the required view angle from one or more thermal images that are obtained from a thermal video or live stream thermal video.

16. A system for determining a view angle of a thermal image from a user and generating a suggestion to enable the user for adaptive positioning of a subject for capturing the thermal image, characterized in that the system comprising:
a storage device; and
a processor retrieving machine-readable instructions from the storage device which, when executed by the processor, enable the processor to:
receive a thermal image of a body of a subject, which represents the temperature distribution on the body of the subject as pixels in the thermal image with a highest temperature value being displayed in a first color and pixels with a lowest temperature value being displayed in a second color, pixels with temperature values between the lowest and highest temperature values being displayed in gradations of color between the first and second colors, wherein the thermal image is captured by a thermal imaging camera, wherein the thermal imaging camera comprising:
an array of sensors that converts infrared energy into electrical signals on a per-pixel basis;
a lens that focuses the infrared energy from the subject's body onto the array of sensors, wherein the array of sensors detects temperature values from the subject's body; and
a specialized processor that processes the detected temperature values into at least one block of pixels to generate the thermal image;
automatically determine a view angle of the thermal image from a user using a view angle estimator;
determine, using a machine learning n angular adjustment to be made to a view position of the thermal imaging camera or a position of the subject by comparing the determined view angle with a required view angle as per thermal imaging protocol when the thermal image does not meet the required view angle as per thermal imaging protocol; and
generate a set of instructions to the user for adjusting the view position of the thermal imaging camera for capturing a new thermal image at the required view angle as per thermal imaging protocol.

17. The system of claim 16, wherein the system provides the new captured thermal image along with determined view angle to the view angle determination unit for automatic breast, segmentation followed by an automatic tumor detection method to detect cancerous tissue and/or non-cancerous tissue within a breast area of the subject.

18. The system of claim 17, wherein the system implements an automatic segmenting technique to segment the breast area of the subject in the thermal image by:
determining an outer side contour of an outline of a boundary of the breast area of the subject from a body silhouette;
determining an inner side boundary of the breast area from the body silhouette and the view angle of the thermal image;
determining an upper boundary of the breast area by determining a lower boundary of an isotherm of axilla of the subject;
determining a lower boundary of the breast area by determining an upper boundary of an isotherm of infra-mammary fold of the person; and
segmenting the breast area of the subject by connecting above determined breast boundaries to segment the breast from surrounding tissue in the thermal image.

19. The system of claim 17, wherein the system implements the automatic segmenting technique to segment the breast area of the subject in the thermal image by:
training a deep learning model by providing a plurality of thermal images as an input and the corresponding segmentation as an output to obtain the trained deep learning model; and
providing the new captured thermal image to the trained deep learning model to predict a final segmentation map.

20. The system of claim 16, wherein the system provides set of instructions to at least one of a robotic arm holding the camera, an electronically controlled camera stand or an electronically controlled rotating chair to automatically positions itself to the suggested angular adjustment for capturing the new thermal image at the required view angle.

* * * * *